(12) United States Patent
Chakravarti et al.

(10) Patent No.: US 9,115,045 B2
(45) Date of Patent: Aug. 25, 2015

(54) METHOD AND SYSTEM FOR PRODUCING METHANOL USING AN OXYGEN TRANSPORT MEMBRANE BASED REFORMING SYSTEM

(71) Applicants: Shrikar Chakravarti, East Amherst, NY (US); Minish M. Shah, East Amherst, NY (US); Raymond Francis Drnevich, Clarence Center, NY (US); Wladimir Y. Sarmiento-Darkin, Amherst, NY (US); Brian R. Kromer, Buffalo, NY (US); Sean M. Kelly, Pittsford, NY (US)

(72) Inventors: Shrikar Chakravarti, East Amherst, NY (US); Minish M. Shah, East Amherst, NY (US); Raymond Francis Drnevich, Clarence Center, NY (US); Wladimir Y. Sarmiento-Darkin, Amherst, NY (US); Brian R. Kromer, Buffalo, NY (US); Sean M. Kelly, Pittsford, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 14/081,403

(22) Filed: Nov. 15, 2013

(65) Prior Publication Data

US 2014/0323599 A1   Oct. 30, 2014

Related U.S. Application Data

(60) Provisional application No. 61/816,330, filed on Apr. 26, 2013.

(51) Int. Cl.
| | | |
|---|---|---|
| *C07C 29/151* | (2006.01) | |
| *C01B 3/38* | (2006.01) | |
| *C01B 13/02* | (2006.01) | |

(52) U.S. Cl.
CPC .............. *C07C 29/1518* (2013.01); *C01B 3/38* (2013.01); *C01B 3/382* (2013.01);

(Continued)

(58) Field of Classification Search
CPC   C07C 29/1518; C07C 31/04; C01B 13/0251; C01B 2203/0233; C01B 2203/0244; C01B 2203/0261; C01B 2203/0833; C01B 2203/141; C01B 2203/148; C01B 3/38; C01B 3/382
USPC .......................................................... 518/704
See application file for complete search history.

(56) References Cited

U.S. PATENT DOCUMENTS

| | | |
|---|---|---|
| 4,650,814 A | 3/1987 | Keller |
| 6,048,472 A | 4/2000 | Nataraj et al. |

(Continued)

FOREIGN PATENT DOCUMENTS

| | | |
|---|---|---|
| EP | 0 926 096 A1 | 6/1999 |
| EP | 0 984 500 A2 | 3/2000 |

(Continued)

OTHER PUBLICATIONS

Friedemann Marschner et al., "Gas Production", Ullmann's Encyclopedia of Industrial Chemistry, Jun. 15, 2000, pp. 1-21, XP002253967.

*Primary Examiner* — Jafar Parsa
*Assistant Examiner* — Amy C Bonaparte
(74) *Attorney, Agent, or Firm* — Ralph J. Mancini

(57) ABSTRACT

A method and system for producing methanol that employs both an oxygen transport membrane (OTM) based reforming system together with a more traditional steam methane reforming (SMR) and/or autothermal (ATR) synthesis gas production system is disclosed. The dual mode system and method for producing the synthesis gas in a methanol production process optimizes the efficiency and productivity of the methanol plant by using the OTM based reforming system as an independent source of synthesis gas. The disclosed methods and systems are configurable either as a retrofit to existing methanol production facilities or as an integrated package into newly constructed methanol production facilities.

16 Claims, 7 Drawing Sheets

(52) U.S. Cl.
CPC .... *C01B 13/0251* (2013.01); *C01B 2203/0233* (2013.01); *C01B 2203/0244* (2013.01); *C01B 2203/0261* (2013.01); *C01B 2203/061* (2013.01); *C01B 2203/0833* (2013.01); *C01B 2203/141* (2013.01); *C01B 2203/148* (2013.01)

(56) References Cited

U.S. PATENT DOCUMENTS

| | | | |
|---|---|---|---|
| 6,110,979 | A | 8/2000 | Nataraj et al. |
| 6,114,400 | A | 9/2000 | Nataraj et al. |
| 6,214,314 | B1 | 4/2001 | Nataraj et al. |
| 6,293,084 | B1 | 9/2001 | Drnevich et al. |
| 6,296,686 | B1 | 10/2001 | Prasad et al. |
| 6,360,524 | B1 * | 3/2002 | Drnevich et al. ............... 60/783 |
| 6,382,958 | B1 | 5/2002 | Bool, III et al. |
| 6,394,043 | B1 | 5/2002 | Bool, III et al. |
| 6,562,104 | B2 | 5/2003 | Bool, III et al. |
| 7,261,751 | B2 | 8/2007 | Dutta et al. |
| 7,470,811 | B2 | 12/2008 | Thiebaut |
| 7,786,180 | B2 | 8/2010 | Fitzpatrick |
| 7,856,829 | B2 | 12/2010 | Shah et al. |
| 8,196,387 | B2 | 6/2012 | Shah et al. |
| 8,262,755 | B2 | 9/2012 | Repasky et al. |
| 8,349,214 | B1 | 1/2013 | Kelly et al. |
| 8,419,827 | B2 | 4/2013 | Repasky et al. |
| 2003/0039608 | A1 | 2/2003 | Shah et al. |
| 2007/0004809 | A1 * | 1/2007 | Lattner et al. ............... 518/700 |
| 2007/0041894 | A1 * | 2/2007 | Drnevich ............... 423/650 |
| 2007/0289215 | A1 | 12/2007 | Hemmings et al. |
| 2007/0292342 | A1 | 12/2007 | Hemmings et al. |
| 2008/0302013 | A1 * | 12/2008 | Repasky et al. ............... 48/127.9 |
| 2009/0120379 | A1 | 5/2009 | Bozzuto et al. |
| 2011/0076213 | A1 | 3/2011 | Carolan et al. |
| 2011/0142722 | A1 | 6/2011 | Hemmings et al. |
| 2013/0009102 | A1 | 1/2013 | Kelly et al. |
| 2014/0183866 | A1 | 7/2014 | Kromer et al. |
| 2014/0319424 | A1 | 10/2014 | Chakravarti et al. |
| 2014/0319427 | A1 | 10/2014 | Chakravarti et al. |
| 2014/0323597 | A1 * | 10/2014 | Stuckert et al. ............... 518/703 |
| 2014/0323598 | A1 * | 10/2014 | Chakravarti et al. ......... 518/703 |

FOREIGN PATENT DOCUMENTS

| | | |
|---|---|---|
| EP | 0 989 093 A2 | 3/2000 |
| EP | 1 504 811 A1 | 2/2005 |
| WO | WO 2013/062413 A1 | 5/2013 |
| WO | WO 2014/107707 A2 | 7/2014 |

* cited by examiner

METHOD AND SYSTEM FOR PRODUCING METHANOL USING AN OXYGEN TRANSPORT MEMBRANE BASED REFORMING SYSTEM

CROSS REFERENCE TO RELATED APPLICATIONS

This application claims priority to and the benefit of U.S. provisional patent application Ser. No. 61/816,330 filed on Apr. 26, 2013, the disclosure of which is incorporated by reference herein.

FIELD OF THE INVENTION

The present invention relates to a method and system for producing methanol using an oxygen transport membrane based reforming system as a source of synthesis gas, and more particularly, a method and system for integrating an oxygen transport membrane based reforming system with a steam methane reformer or other conventional synthesis gas production means and further with the methanol synthesis system and process.

BACKGROUND

The methanol production process generally involves directing a compressed synthesis gas comprising hydrogen, carbon monoxide and carbon dioxide at an elevated temperature and pressure to a methanol converter reactor containing one or more beds of a methanol synthesis catalyst such as a copper and zinc oxide catalyst. The carbon monoxide and carbon dioxide in the synthesis gas react with the hydrogen to form methanol across the catalyst. The methanol synthesis process is usually operated in a loop where a portion of the compressed synthesis gas is converted to methanol each pass through the methanol converter reactor. Methanol product is recovered by cooling the methanol product gas stream to a temperature below the dew point of the methanol such that crude methanol and water condense out, with the remaining gas being recycled through the methanol converter reactor. The crude methanol and water produced in the methanol converter reactor are typically reduced in pressure in a let-down or "flash" vessel. Since most crude methanol contains a large range of impurities, the crude methanol must be purified so as to remove such impurities to produce methanol of chemical grade quality. The preferred technique used for methanol purification is a distillation process.

Synthesis gas is typically characterized by the stoichiometric ratio (H2−CO2)/(CO+CO2), often referred to as the module. A module of about 2.0 defines the desired stoichiometric ratio of synthesis gas for the production of methanol. Other important properties of the synthesis gas in methanol production include the carbon monoxide to carbon dioxide ratio and the concentration of inerts in the synthesis gas. A high carbon monoxide to carbon dioxide ratio typically increases the reaction rate and the achievable per pass conversion while concurrently decreases the formation of water thereby reducing the catalyst deactivation rate. A high concentration of inerts in the synthesis gas, such as methane, argon, nitrogen, etc. typically lowers the partial pressure of the active reactants. Since the methanol conversion reaction is exothermic, lower temperatures favor conversion of the synthesis gas to methanol. Pressure will also affect the methanol conversion reaction, with increasing pressure also favoring methanol formation.

In many methanol production facilities, the incoming compressed synthesis gas is often mixed with recycled unreacted gas stream to form the synthesis gas stream that is supplied to the methanol converter reactor. A portion of the unreacted gas stream may be purged to prevent the buildup of inerts in the methanol converter reactor. The amount of purge flow typically varies anywhere from 1% to 6% of the total unreacted gas stream and often depends on the amount of inerts in the incoming synthesis gas, with higher level of inerts generally requiring higher purge flows and lower level of inerts generally requiring lower purge flows.

The challenge facing many methanol producers is to optimize the integration of the synthesis gas production or front-end of the methanol plant with the methanol synthesis or back-end of the methanol plant. Integration of the front-end synthesis gas production with the methanol synthesis or back-end of the methanol plant has to date focused on use of the purge flow from the methanol synthesis section in the synthesis gas production section and use of heat recovery systems that efficiently utilize excess heat generated in both sections of the methanol plant.

The purge flow containing unconverted hydrogen and/or methane slip can also be recovered and recycled back to the front-end or synthesis gas producing portion of the methanol plant. Similarly, the excess heat generated in the exothermic methanol conversion reaction is typically used to pre-heat the synthesis gas feed to the methanol synthesis section, to generate saturated steam, to pre-heat the reformer feed streams and/or to heat boiler feed water used in the synthesis gas production process. Some of the prior art uses of the purge stream include use of the hydrogen and/or methane slip in the purge stream as a feed or source of fuel to be used in the front-end steam methane reforming (SMR), partial oxidation (POx), autothermal reforming (ATR) processes. Other prior art has suggested the recovery of hydrogen from the purge stream and mixing the recovered hydrogen with the synthesis gas to improve the module of synthesis gas for methanol production.

As used herein, steam methane reforming (SMR) is a catalytic conversion of natural gas, including methane and light hydrocarbons, to synthesis gas containing hydrogen and carbon monoxide by reaction with steam. The reactions are endothermic, requiring significant amount of energy input. The steam methane reforming process is carried out at high temperatures with the catalyst inside tubes within a fired furnace. The amount of steam used is in excess of the reaction stoichiometry requirements, as required to prevent the catalyst from coking. No oxygen is used in steam methane reforming.

Partial oxidation, on the other hand, is a non-catalytic process where a sub-stoichiometric amount of oxygen is allowed to react with the natural gas creating steam and carbon dioxide at high temperatures. The residual methane is reformed through reactions with the high temperature steam and carbon dioxide to produce synthesis gas. Autothermal reforming is a variant of the partial oxidation process, but which uses a catalyst to permit reforming to occur at lower temperatures than the POx process.

Many synthesis gas generation methods also employ pre-reforming and secondary reforming. When the feedstock contains significant amounts of heavy hydrocarbons, SMR and ATR processes are typically preceded by a pre-reforming step. As generally known in the art, pre-reforming is a catalyst based process for converting higher hydrocarbons to methane, hydrogen, carbon monoxide and carbon dioxide. The reactions involved in pre-reforming are endothermic. Most pre-reformers operate adiabatically, and thus the pre-reformed feedstock leaves at a much lower temperature than the feedstock entering the pre-reformer. A secondary reforming process conventionally refers to an autothermal reforming process that is fed product from a SMR process. Thus, the feed to a secondary reforming process is primarily synthesis gas from the SMR. Depending on the end application, some natural gas may bypass the SMR process and be directly introduced into the secondary reforming process. Also, when a SMR process is followed by a secondary reforming process, the SMR may operate at a lower temperature, e.g. 650° C. to 800° C. versus 850° C. to 950° C.

A synthesis gas with a module less than about 2.0 signifies that the synthesis gas is deficient in hydrogen for the production of methanol. In such a case, the hydrogen will be consumed in the methanol synthesis reaction while a substantial portion of the carbon monoxide and carbon dioxide remain unreacted leading to a recycle stream of unreacted gas which has very high levels of carbon monoxide and carbon dioxide but is low in hydrogen. This causes several disadvantages including higher volume of catalysts and increased production of unwanted by-products, namely higher alcohols and ketones. The module of crude synthesis gas is often determined by the reforming process used with reforming processes such as partial oxidation (POx) and autothermal reforming (ATR) generally producing hydrogen deficient synthesis gas.

To remedy the hydrogen deficiency of synthesis gas, it has been suggested to recover hydrogen from the purge stream using a hydrogen recovery unit such as a hydrogen pressure swing adsorption (PSA) unit or hydrogen separation membrane. The recovered hydrogen is recycled back into the synthesis gas so that the gas within the methanol synthesis loop is significantly more hydrogen rich than the originally produced synthesis gas. An alternative method to remedy the hydrogen deficiency of synthesis gas is to take a side-stream of the original produced synthesis gas and recover hydrogen from it using a hydrogen pressure swing adsorption (PSA) unit or hydrogen separation membrane and feeding the recovered hydrogen back into the synthesis gas directed to the methanol synthesis reactor. See U.S. Pat. Nos. 7,786,180; 7,470,811; and 4,650,814. U.S. Pat. No. 7,786,180 likely represents the closest prior art in the field of methanol synthesis where hydrogen is recovered using a hydrogen recovery unit from both the purge gas and a portion of the original synthesis gas or make up gas. The recovered hydrogen is simply added to the synthesis gas mixture that is directed to the methanol synthesis reactor.

However, the above-identified solutions are limited to addressing the hydrogen deficiency of synthesis gas and are customized or tailored for use with conventional reforming processes such as steam methane reforming (SMR), partial oxidation (POx), autothermal reforming (ATR) or combinations thereof.

As can be appreciated, these conventional methods of producing a synthesis gas are expensive and involve complex installations. In order to overcome the complexity and expense of such installations it has been proposed to generate the synthesis gas within reactors that utilize an oxygen transport membrane to supply oxygen and thereby generate the heat necessary to support endothermic heating requirements of the steam methane reforming reactions. See, for example, U.S. Pat. Nos. 6,048,472; 6,110,979; 6,114,400 and 6,296,686. However, none of these oxygen transport membrane based reforming arrangements adequately integrate the downstream process with the front-end reforming process in a manner that improves the productivity and cost effectiveness of a methanol production facility.

What is needed, therefore, are advances in methanol plant operations, and more particularly advances in the integration of the synthesis gas production with the methanol synthesis or back-end of the methanol plant where some or all of the synthesis gas is produced using an oxygen transport membrane based reforming systems.

SUMMARY OF THE INVENTION

The present invention may be characterized as a method for producing methanol comprising the steps of: (i) producing a first stream of synthesis gas in a SMR or ATR by reforming a first hydrocarbon feed stream and a source of steam in the presence of a catalyst; (ii) producing a second stream of synthesis gas in an oxygen transport membrane based reforming system by reforming a combined feed stream in the presence of a reforming catalyst and heat generated from reaction of a hydrogen containing stream contacting a permeate side of an oxygen transport membrane and an oxygen permeate produced by the oxygen transport membrane from an oxygen containing feed stream, the reaction producing a reaction product stream and heat, wherein the combined feed stream comprises a second hydrocarbon feed stream, the reaction product stream, and steam; (iii) combining the first stream of synthesis gas and the second stream of synthesis gas to form a combined synthesis gas product stream; (iv) directing the combined synthesis gas product stream to a methanol synthesis reactor; (v) synthesizing the combined synthesis gas product stream into crude methanol; (vi) recovering unconverted hydrogen and methane slip during the methanol synthesis; and (vii) recycling a portion of the unconverted hydrogen and methane slip recovered during the methanol synthesis to the oxygen transport membrane based reforming system; and purifying the crude methanol to a finished methanol product.

Preferably, the combined feed stream used to produce the second synthesis gas stream is preferably at a moderate pressure of between about 100 psia and 250 psia, has a steam to carbon ratio between about 1.5 and 3.0, and a temperature between about 550° C. and 800° C. When the feed stream is reacted in the oxygen transport membrane based reforming system produces the second stream of synthesis gas having a module of between about 1.5 and 2.2; a methane slip of less than about 4.5 percent by volume; and a hydrogen to carbon monoxide ratio of between about 2.8 and 3.8.

The module of combined synthesis gas stream that is directed to the methanol synthesis reactor is preferably between about 2.0 to 2.8. Also, a portion of the excess or unconverted hydrogen recovered during methanol synthesis is preferably recycled to the oxygen transport membrane based reforming system to: (i) form all or a part of the hydrogen containing stream contacting the permeate side of the oxygen transport membrane; (ii) be used as a fuel to heat the oxygen containing feed stream upstream of the oxygen transport membrane; or (iii) used to condition the hydrocarbon feed stream. In some embodiments, a portion of the excess or unconverted hydrogen recovered during methanol synthesis may also be recycled to the SMR or ATR system.

BRIEF DESCRIPTION OF THE DRAWINGS

While the specification concludes with claims distinctly pointing out the subject matter that applicants regard as their invention, it is believed that the invention will be better understood when taken in connection with the accompanying drawings in which:

For the sake of avoiding repetition, some of the common elements in the various Figures utilize the same numbers where the explanation of such elements would not change from Figure to Figure.

DETAILED DESCRIPTION

Figure 1:
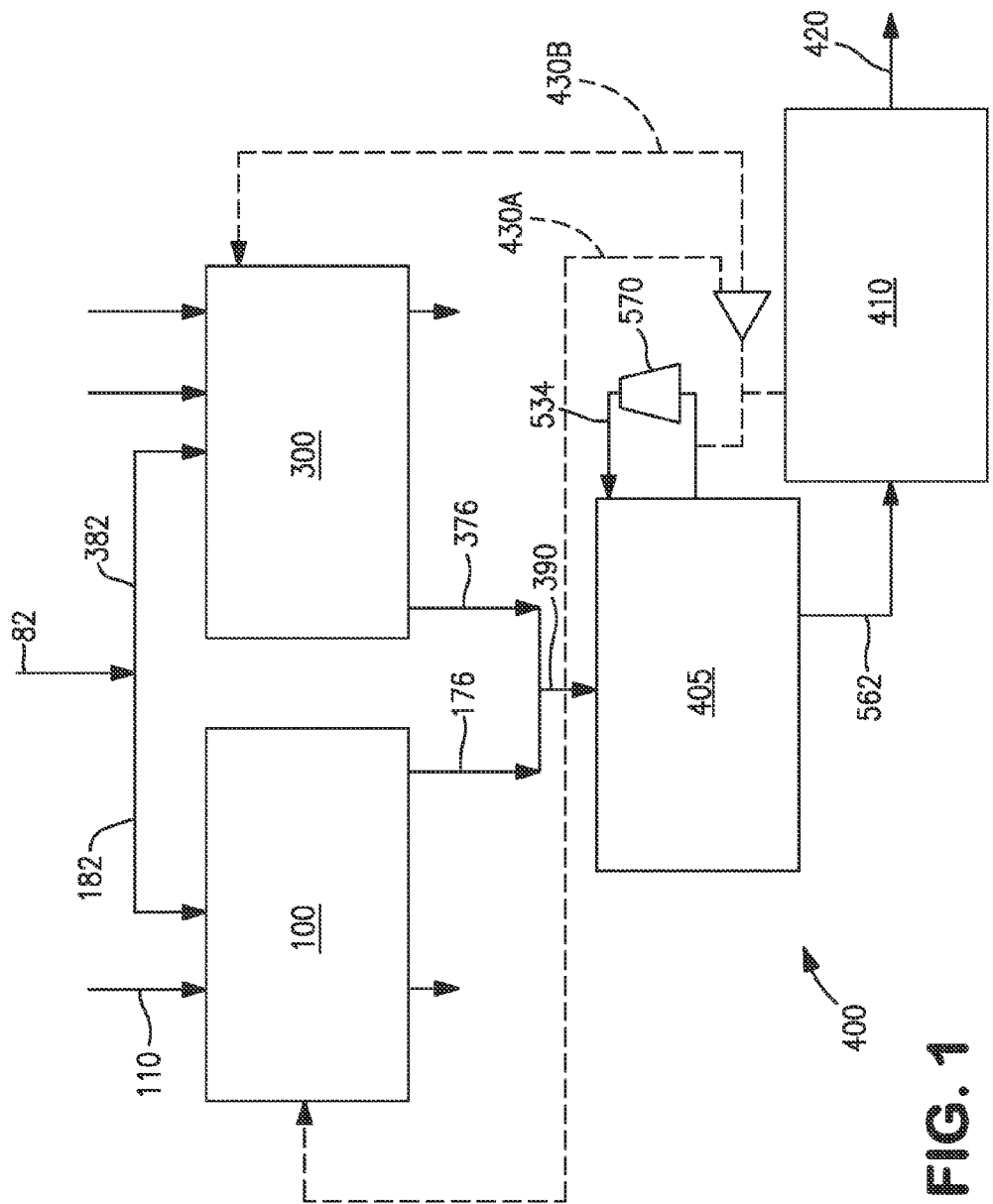
FIG. 1 is a schematic illustration of a methanol production process employing an oxygen transport membrane based reforming system and a conventional synthesis gas generation system, (e.g. SMR, ATR, POx, etc.) in accordance with the present invention.

A preferred configuration or arrangement of coupling an oxygen transport membrane based reforming system to a methanol production process is shown in FIG. 1. As seen therein, the synthesis gas supplied to the methanol synthesis and purification system 400 is a combined synthesis gas stream 390 comprising the synthesis gas product stream 176 produced by the oxygen transport membrane based reforming system 100 and a synthesis gas stream 376 produced from a hydrocarbon feed 382 and a conventional synthesis gas generation system 300 such as a steam methane reformer (SMR); combined reformer; or autothermal reformer (ATR). In this arrangement, the hydrocarbon containing stream 182 is received by the oxygen transport membrane based reforming system 100, as generally described above with reference to FIGS. 2-4. The two hydrocarbon feed streams 182, 382 may be independent streams or, as illustrated, may originate from a common hydrocarbon feed 82.

The combined synthesis gas stream 390 is synthesized into crude methanol 562 in a methanol converter reactor 405 and subsequently purified in a methanol purification system 410 into the methanol product 420. To enhance the overall efficiency of the methanol plant, a portion of the unreacted gas stream is usually recycled to the methanol conveyer reactor 405 via a circulator or compressor 570. In addition, purge streams 430A, 430B comprising unreacted hydrogen and methane slip are recycled from the methanol synthesis and purification system 400 to the oxygen transport membrane based reforming system 100 or the conventional synthesis gas generation system 300 or both. This particular coupling arrangement, schematically shown in FIG. 1, is most suitable for the retrofit of existing methanol production plants having a conventional synthesis gas production system, and where the oxygen transport membrane based reforming system is constructed as a retrofit to the existing methanol production plant and integrated therein.

OTM Based Reforming Reactor and System

Figure 2:
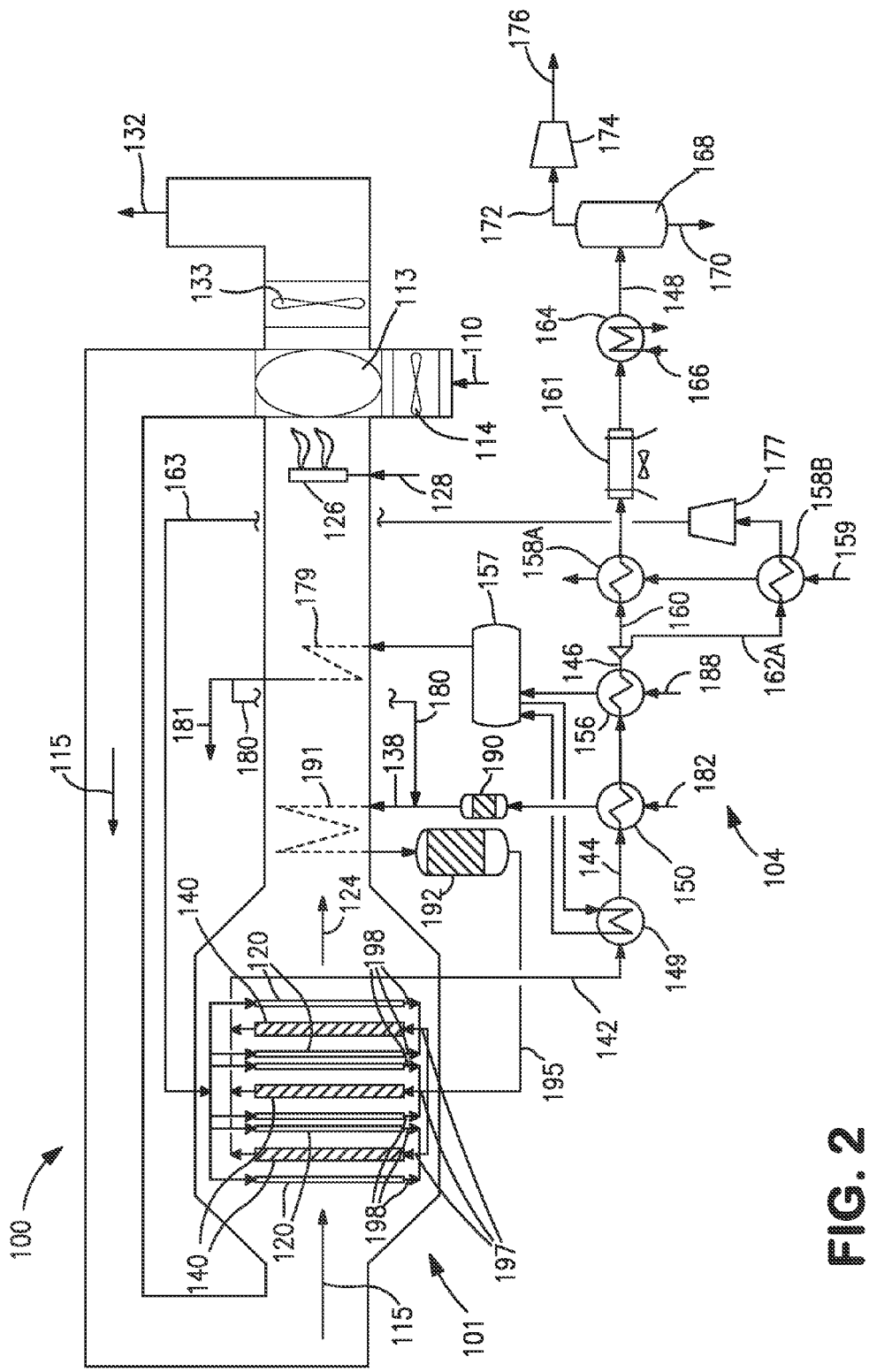
FIG. 2 is a schematic illustration of an embodiment of an oxygen transport membrane based reforming system in accordance with the present invention.

Turning now to FIG. 2, there is shown a schematic illustration of an embodiment of an oxygen transport membrane based reforming system 100 in accordance with the present invention. As seen therein, an oxygen containing stream 110, such as air, is introduced to the system by means of a blower or fan 114 into a heat exchanger 113 for purposes of preheating the oxygen containing stream 110. Heat exchanger 113 is preferably a high efficiency, cyclic and continuously rotating regenerator disposed in operative association with the oxygen containing stream 110 and the heated retentate stream 124. The heated and oxygen depleted retentate stream 124 can optionally be introduced into a duct burner region containing duct burner 126 and used to support combustion of a supplemental fuel stream 128 to produce supplemental heat introduced into the continuously rotating regenerator 113 to pre-heat the oxygen containing stream 110. Alternatively, the duct burner may also be disposed directly in the duct leaving heat exchanger 113 to pre-heat the oxygen containing stream 110. Exhaust stream 132 from heat exchanger 113 is discharged.

The heated oxygen containing stream 115 is then directed via the intake duct to the oxygen transport membrane elements 120 incorporated into the oxygen transport membrane reactor 101. Each of the oxygen transport membrane elements 120 are preferably configured as a multilayered ceramic tube capable of conducting oxygen ions at an elevated operational temperature, wherein the retentate side of the oxygen transport membrane elements 120 is the exterior surface of the ceramic tubes exposed to the oxygen containing stream and the permeate side is the interior surface of the ceramic tubes. Although only six oxygen transport membrane elements 120 are illustrated in close proximity to three catalytic reforming tubes 140, as would occur to those skilled in the art, there could be many of such oxygen transport membrane elements and many catalytic reforming tubes in each oxygen transport membrane assembly. Likewise, there would be multiple oxygen transport membrane assemblies used in an industrial application of the oxygen transport membrane reactor 101.

A hydrogen containing stream is also introduced into the permeate side of the oxygen transport membrane elements 120 and is oxidized though reaction with the permeated oxygen to produce a reaction product stream 198 and heat. As described in more detail below, the hydrogen containing stream is preferably a recycled portion of the produced synthesis gas 163. As a result of the separation of the oxygen and the reaction occurring at the permeate side of oxygen transport membrane elements 120, a heated and oxygen depleted retentate stream 124 is also formed.

The reaction of the hydrogen containing stream or recycled synthesis gas stream 163 at the permeate side of the oxygen transport membrane element 120 produces heat. Radiation of this heat together with the convective heat transfer provided by heated retentate stream 124 heats the catalytic reactor tubes 140 to supply the endothermic heating requirements of the steam methane reforming occurring in catalytic reactor tubes 140. As the heated retentate stream 124 exits the oxygen transport membrane based reforming system 100, it also heats a reformer feed stream 138 to a temperature between about 475° C. and 650° C. via indirect heat transfer using one or more coils 191 disposed in the retentate duct such that the oxygen depleted retentate stream 124 heats the feed streams passing through the coils 191.

The hydrocarbon containing feed stream 182 to be reformed is preferably natural gas. Depending on the supply pressure, the natural gas feed is compressed or let down to the desired pressure via a compressor or valve arrangement (not shown) and then preheated in heat exchanger 150 that serves as a fuel preheater. Also, since the natural gas typically contains unacceptably high level of sulfur species, the natural gas feed stream 182 undergoes a sulfur removal process such as hydro-treating, via device 190, to reduce the sulfur species to $H_2S$, which is subsequently removed in a guard bed using material like ZnO and/or CuO. To facilitate the desulfurization, a small amount of hydrogen or hydrogen-containing gas is added (not shown) to the natural gas feed stream 182. The hydro-treating step also saturates any alkenes present in the hydrocarbon containing feed stream. Further, since natural gas generally contains higher hydrocarbons that will break down at high temperatures to form unwanted carbon deposits that adversely impact the reforming process, the natural gas feed stream 182 is pre-reformed in an adiabatic pre-reformer 192, which converts higher hydrocarbons to methane, hydrogen, carbon monoxide, and carbon dioxide. Pre-reformers are typically catalyst-based systems. In the case of heated pre-reforming, it is contemplated that the catalyst based pre-reformer be thermally coupled with the oxygen transport membrane based reforming system.

In the illustrated embodiment, the above-described heated reaction product stream 198 is combined with the pre-reformed reformer feed stream 195 to produce a combined feed stream 197 that contains steam and hydrocarbons. This combined feed stream is introduced into the catalytic reactor tubes 140 where the combined feed stream 197 is subjected to steam methane reforming to produce a synthesis gas stream 142. The temperature of the combined feed stream 197 is between about 550° C. and 800° C., and more preferably between about 600° C. and 800° C. Steam 180 may also be added to the combined feed stream 197, or the preheated pre-reformed reformer feed stream 195, as required, to adjust the temperature of stream 197 as well as the steam to carbon ratio of stream 197 to between about 1.5 and 3.0, and more preferably to steam to carbon ratio between about 2.0 and 2.8. The steam is preferably superheated steam 180 between about 300 psia and 1200 psia and between about 300° C. and 600° C. and heated by means of indirect heat exchange with the heated retentate stream 124 using steam coils 179 disposed in the retentate duct. The superheated steam 180 is preferably added to the hydrocarbon containing feed stream 182 upstream of the pre-reformer 192 to adjust the steam to carbon ratio and final temperature of the combined feed stream 197. Also, as described in more detail with reference to FIG. 7, to reduce the methane slip and optimize the economic performance of the oxygen transport membrane based reforming system in a methanol production process, the oxygen transport membrane reactor 101 should preferably be maintained at an exit pressure of less than or equal to about 250 psia.

The synthesis gas stream 142 produced by the oxygen transport membrane based reforming system 100 generally contains hydrogen, carbon monoxide, steam, carbon dioxide and other constituents such as unconverted methane. Heat exchange section 104 is designed to cool the produced synthesis gas stream 142 and recycle a portion of the synthesis gas stream 162A to form all or a part of the hydrogen containing stream 163. In this illustrated embodiment, the synthesis gas stream 142 is preferably cooled before recycling such stream using a synthesis gas recycle compressor 177 or other blower means. The heat exchange section 104 is also designed such that in cooling the synthesis gas stream 142, various feed streams are preheated and process steam is also generated.

The initial cooling of synthesis gas stream 142 is accomplished with steam generation in a process gas boiler (PG boiler) 149 coupled to steam drum 157 and designed to reduce the temperature of the cooled synthesis gas 144 to about 400° C. or less. As illustrated in FIG. 2, the initially cooled synthesis gas stream 144 is successively further cooled in a heat exchange network that includes hydrocarbon feed preheater 150, economizer 156, feed water heaters 158A and 158B, synthesis gas cooler 161 and water cooled heat exchanger 164.

The initially cooled synthesis gas stream 144 is directed to the natural gas feed preheater 150 to heat the natural gas feed stream 182 and then is directed to the economizer 156 to heat boiler feed water 188. The boiler feed water stream 188 is preferably pumped using a feed water pump (not shown), heated in economizer 156 and sent to steam drum 157.

The cooled synthesis gas stream 146 is then divided into a first portion 160 and a second or recycled portion 162A. First portion 160 is further cooled in a series of steps including a feed water heater 158A, used to heat feed water stream 159, followed by a synthesis gas cooler 161 and a subsequent water cooled heat exchanger 164 cooled via a separate cooling water stream 166. The heated feed water 159 is directed to a de-aerator (not shown) that provides boiler feed water 188. The resulting fully cooled synthesis gas stream 148 is then introduced into a knock-out drum 168 from which a condensate stream 170 is drained to produce a fully cooled synthesis gas stream 172. The fully cooled synthesis gas stream 172 is optionally compressed in a synthesis gas compressor 174 to produce a synthesis gas product 176.

The second or recycled portion 162A of the initially cooled synthesis gas stream 144 is directed to a second feed water heater 158B, used to heat feed water stream 159, and this cooled recycle synthesis gas stream 163 is recirculated back to the permeate side of the oxygen transport membrane element 120 by means of a recycle compressor 177. Also note that any superheated steam not added or used in natural gas feed 182 or recycle synthesis gas stream 163 is exported steam 181 that may be used for power generation.

When customized for a methanol production process, the oxygen transport membrane produced synthesis gas should have a module of between about 1.5 and 2.0. In addition, such produced synthesis gas stream ideally has a methane slip of less than about 4.5 percent by volume where the exit pressure of the oxygen transport membrane based reforming system is 250 psia or less.

Figure 3:
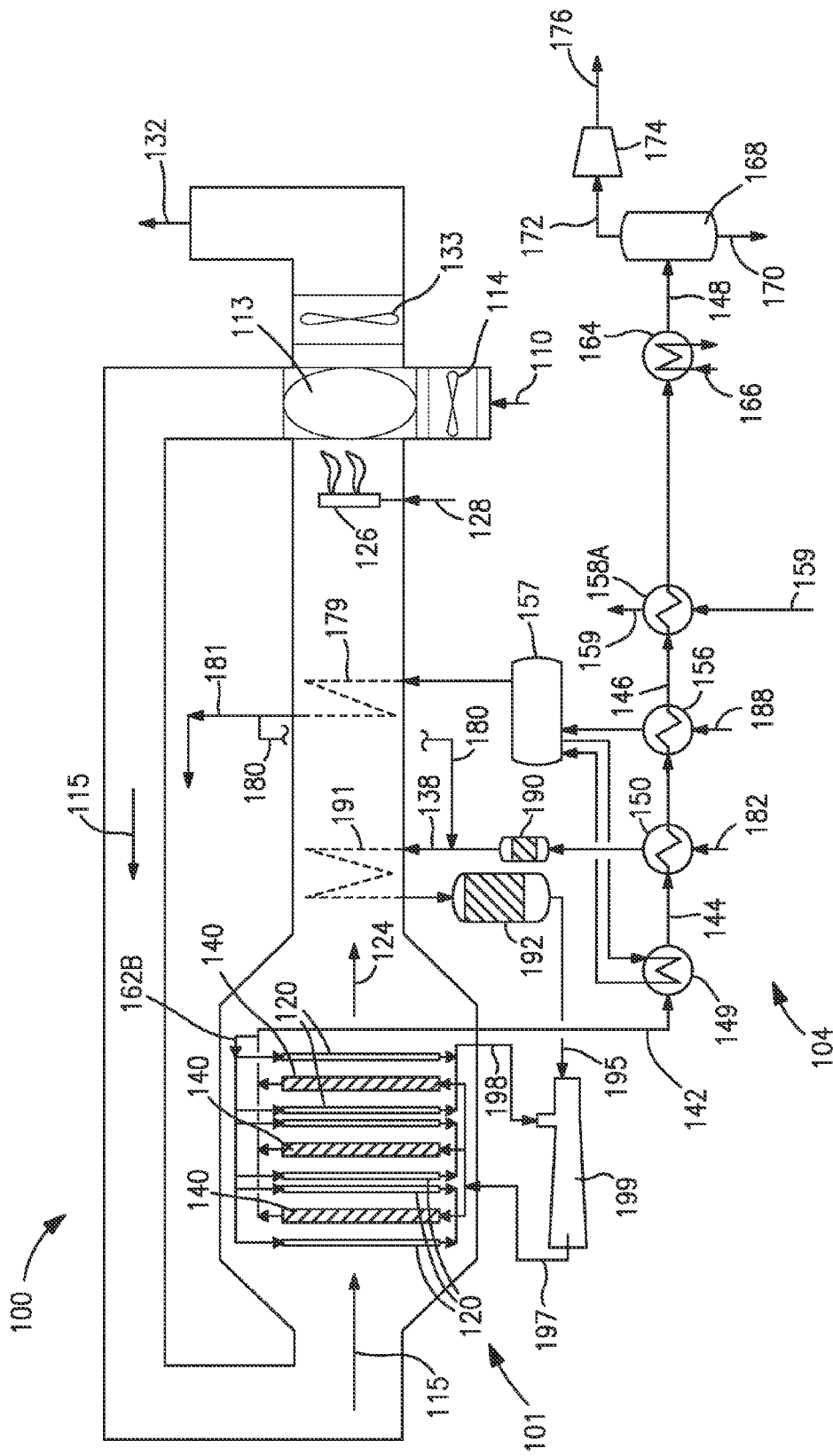
FIG. 3 is a schematic illustration of an alternate embodiment of an oxygen transport membrane based reforming system and system.

Turning now to FIG. 3, there is shown a schematic illustration of an alternate embodiment of an oxygen transport membrane based reforming system. In many regards, this embodiment is similar to the embodiment of FIG. 2 and, for sake of brevity, the description of the common aspects of the two embodiments will not be repeated here, rather, the following discussion shall focus on differences between FIG. 2 and FIG. 3.

The primary difference between the embodiments in FIG. 2 and FIG. 3 is the use of a hot synthesis gas recycle 162B in FIG. 3 embodiment in lieu of the cold gas recycle 162A in the embodiment of FIG. 2. As a result, the heat exchange section 104 in FIG. 3 is designed to only cool the produced synthesis gas stream 142 and need not recycle a portion of the cold synthesis gas stream 162A. By using the hot synthesis gas recycle 162A, there is no need to use the synthesis gas recycle compressor 177 or the second feed water heater 158B, used to heat feed water stream 159 potentially further reducing the capital cost of the oxygen transport membrane based reformer reactor and system.

The hot synthesis gas recycle involves recycling a portion of the heated synthesis gas stream 142 exiting the catalyst reforming tubes 140 or reactor and directing the hot recycled synthesis gas 162B to the permeate side of the oxygen transport membrane elements 120 to react the portion of heated synthesis gas stream 162B with the oxygen permeate to generate the heated reaction product stream and radiant heat. The temperature of the hot synthesis recycled gas is preferably above 800° C. so as to avoid problems associated with metal dusting corrosion.

The hot synthesis gas stream 162B is driven or pulled to the permeate side of the oxygen transport membrane elements 120 by means of an ejector, eductor or venturi based device 199 operatively coupled to the permeate side of the oxygen transport membrane elements 120. By suctioning the streams at the permeate side of the oxygen transport membrane elements 120 into the ejector, eductor or venturi based device 199 with a motive fluid comprising the pre-reformed reformer feed stream 195, the reaction product stream 198 mixes with the pre-reformed reformer feed stream 195 to produce the combined feed stream 197, preferably having a steam to carbon ratio between about 1.5 and 3.0 and a temperature between about 550° C. and 800° C. Essentially, device 199 moves the lower pressure hot synthesis gas recycle stream 162B to the higher pressure combined feed stream 199.

Figure 4:
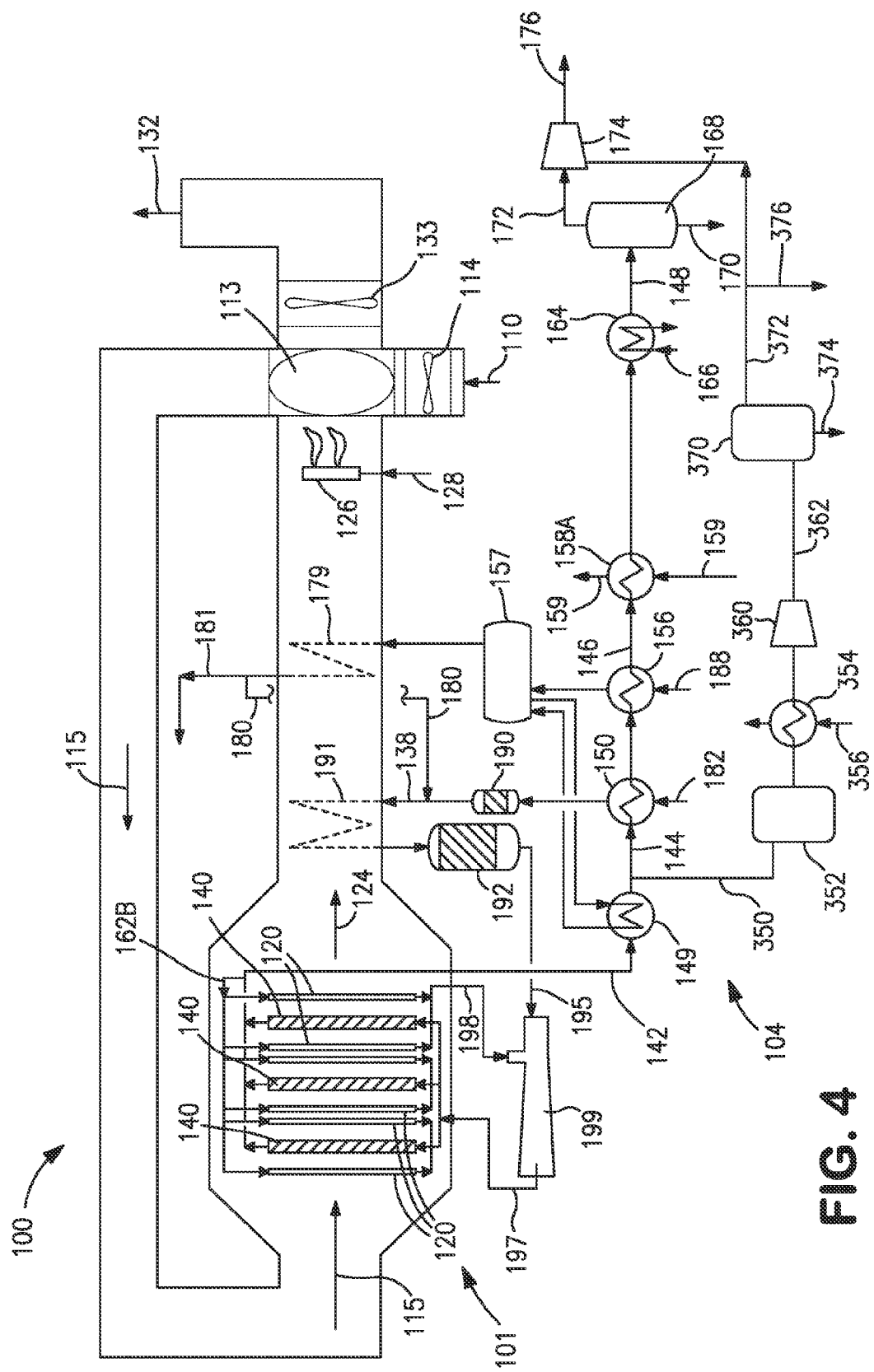
FIG. 4 is a schematic illustration of yet another embodiment of an oxygen transport membrane based reforming system in accordance with the present invention for a methanol production facility, where the oxygen transport membrane based reforming system is the only or a primary source of synthesis gas supply.

Turning now to FIG. 4, there is shown a schematic illustration of yet another alternate embodiment of an oxygen transport membrane based reforming system. In many regards, this illustrated embodiment is similar to the embodiments shown in FIG. 2 and FIG. 3. Thus, for sake of brevity; the description of the common aspects of the embodiments will not be repeated here. Rather, the following discussion shall focus on the differences present in the embodiment of FIG. 4.

The primary difference between the embodiments in FIG. 3 and FIG. 4 is the addition of downstream processing of the cooled synthesis gas in the embodiment of FIG. 4. As seen therein, a portion of the initially cooled synthesis gas 350 is diverted to a synthesis gas conditioning system. This diverted portion of the cooled synthesis gas stream 350 is roughly between about 5% and 25% of the synthesis gas stream 142.

The diverted portion of the cooled synthesis gas stream 350 is subjected to a water gas shift reaction in reactor 352 and subsequently cooled in heat exchanger 354 using cooling water or boiler feed water and then compressed in a synthesis gas compressor 360. Alternatively, heat exchanger 354 could instead be used to preheat a portion of the natural gas feed 182. The compressed gas feed stream 362 is directed to a hydrogen pressure swing adsorption (PSA) unit 370 which takes the compressed feed stream 362 and produces a higher purity hydrogen stream 372 at or near the feed pressure while the carbon oxides, methane and other impurities are rejected at lower pressure tail gas stream 374. Stream 374 may be recycled to use with the duct burners 126 while the higher pressure and higher purity hydrogen stream 372 is recombined with the non-diverted portion of the synthesis gas stream 172, preferably at some point mid-stage point within the synthesis gas compressor 174. By re-combining the higher purity hydrogen stream 372 with the non-diverted portion of the synthesis gas stream 172, one can adjust the module of the final synthesis gas product to about 2.0 to 2.2, the preferable range for methanol production or other synthesis gas characteristics such as hydrogen to carbon monoxide ratio, etc. It may also be possible to combine a portion or all of the purge 430A (see FIG. 1) from the methanol loop with stream 362 prior to feeding the PSA unit 370.

The embodiment shown in FIG. 4 is particularly applicable to use in a methanol production facility, where the oxygen transport membrane based reforming system is the only or primary source of synthesis gas supply to the methanol synthesis process.

Figure 5:
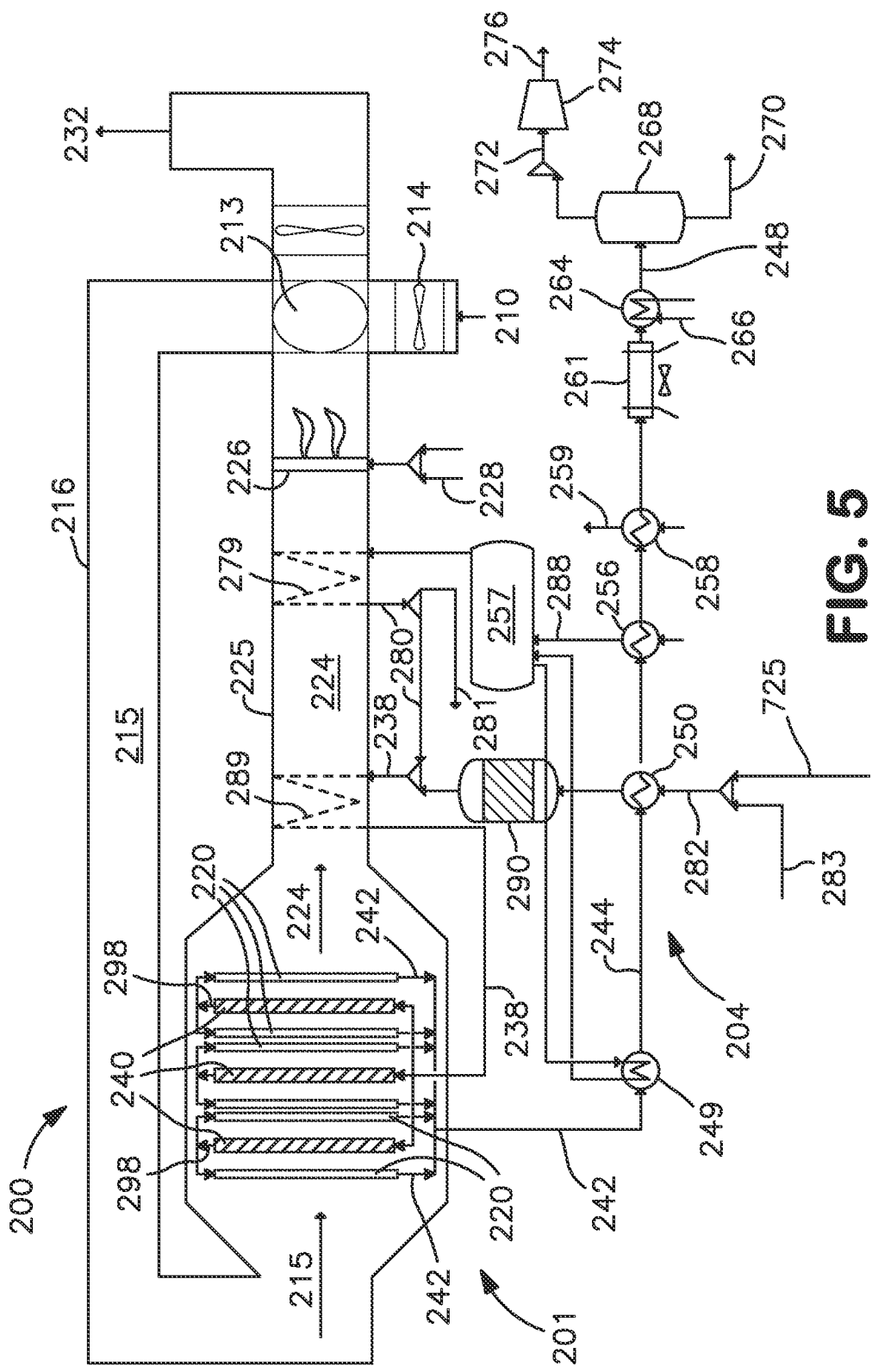
FIG. 5 is a schematic illustration of an alternate embodiment of an oxygen transport membrane based reforming system configured to carry out a primary reforming process and a secondary reforming process for production of synthesis gas.

FIG. 5 provides a schematic illustration of an alternate embodiment of an oxygen transport membrane based reforming system 200 in accordance with the present invention. As seen therein, an oxygen containing stream 210, such as air, is introduced to the system by means of a forced draft (FD) fan 214 into a heat exchanger 213 for purposes of preheating the oxygen containing feed stream 210. Heat exchanger 213 is preferably a high efficiency, cyclic and continuously rotating ceramic regenerator disposed in operative association with the oxygen containing feed stream 210 and the heated retentate stream 224. The ceramic regenerator 213 which heats the incoming air feed stream 210 to a temperature in the range of about 850° C. to 1000° C.

The oxygen depleted air leaves the oxygen transport membrane reforming tubes as a heated retentate stream 224 at the same or slightly higher temperature than the heated air feed stream 215. Any temperature increase, typically <30° C., is attributable to the portion of energy generated by the oxidizing reaction of hydrogen and carbon monoxide in the oxygen transport membrane tubes and transferred by convection to the air stream. The heated, oxygen depleted retentate stream 224 is first used to heat the mixed feed stream to a temperature between 450° C. and 650° C., and more preferably to a temperature between 525° C. and 600° C., and used to further heat the superheated steam.

The temperature of this oxygen depleted retentate stream 224 preferably needs to be then increased back to a temperature between about 1050° C. and 1200° C. prior to being directed to the ceramic heat exchanger or regenerator 213. This increase in temperature of the retentate stream 224 is preferably accomplished by use of a duct burner 226, which facilitates combustion of a supplemental fuel stream 228 using some of the residual oxygen in the retentate stream 224. It is conceivable that the mixed feed heater and steam superheater could alternatively be located in a separate fired heater (not shown). In that case, the fuel requirements of the duct burner 226 will be substantially less. In the ceramic heat exchanger or regenerator 213, the heated, oxygen depleted retentate stream provides the energy to raise the temperature of the incoming feed air stream from ambient temperature to a temperature between about 900° C. and 1000° C. The resulting cold retentate stream exiting the ceramic heat exchanger, typically containing less than 5% oxygen, leaves the oxygen transport membrane based reforming system 200 as exhaust gas 232 at a temperature of around 150° C.

The oxygen transport membrane based reforming system 200 comprises two sets of reforming tubes, including primary reforming tubes 240 where the primary reforming occurs and oxygen transport membrane tubes 220 where the secondary reforming occurs. Although only six secondary reforming oxygen transport membrane tubes 220 are illustrated in close proximity to three primary reforming tubes 240, as would occur to those skilled in the art, there could be many of such secondary reforming oxygen transport membrane tubes and many primary reforming tubes in each oxygen transport membrane assembly. Likewise, there would be multiple oxygen transport membrane assemblies used in an industrial application of the oxygen transport membrane based reforming system 200.

The heated oxygen containing stream 215 is directed via the intake duct 216 to a plurality of secondary reforming oxygen transport membrane tubes 220 incorporated into the oxygen transport membrane reactor 201. The secondary reforming oxygen transport membrane tubes 220 are preferably configured as multilayered ceramic tubes capable of conducting oxygen ions at an elevated operational temperature, wherein the retentate side of the secondary reforming oxygen transport membrane tubes 220 is the exterior surface of the ceramic tubes exposed to the heated oxygen containing stream 215 and the permeate side is the interior surface of the ceramic tubes. Within each of the secondary reforming oxygen transport membrane tubes 220 are one or more catalysts that facilitate secondary reforming.

The hydrocarbon containing feed stream 282, preferably natural gas, to be reformed is typically preheated to around 370° C., as described in more detail below. As natural gas typically contains unacceptably high level of sulfur species, some hydrogen gas 725 is added prior to desulfurization. The mixture 283 of the hydrogen gas 725 and hydrocarbon containing feed stream 282 is heated in heat exchanger 250 that serves as a pre-heater and then undergoes a sulfur removal process via device 290 such as hydro-treating to reduce the sulfur species to $H_2S$, which is subsequently removed in a guard bed using material like ZnO and/or CuO. The hydro-treating step also saturates any alkenes present in the hydrocarbon containing feed stream. Although not shown, the heated feed stream 282 may also undergo pre-reforming step an adiabatic pre-reformer, which converts higher hydrocarbons to methane, hydrogen, carbon monoxide, and carbon dioxide or a heated pre-reforming step. In the case of heated pre-reforming, it is contemplated that the catalyst based pre-reformer be thermally coupled with the oxygen transport membrane based reforming system.

Superheated steam 280 is added to the pre-treated natural gas and hydrogen feed stream, as required, to produce a mixed feed stream 238 with a steam to carbon ratio between about 1.0 and 2.5, and more preferably between about 1.2 and 2.2. The superheated steam 280 is preferably between about 300 psia and 1200 psia and between about 300° C. and 600° C. and heated by means of indirect heat exchange with the heated retentate stream 224 using steam coils 279 disposed in the retentate duct 225. Any superheated steam 280 not added or used in the natural gas and hydrogen feed 282 is exported steam 281 used for power generation. The mixed feed stream 238 is heated, by means of indirect heat exchange with the heated retentate stream using coils 289 disposed in the retentate duct 225, to preferably between about 475° C. and 650° C., and more preferably between about 550° C. and 600° C.

The heated mixed feed stream 238 is then sent to the reforming tubes 240, which contain conventional reforming catalyst. The temperature of the partially reformed hydrogen-rich synthesis gas 298 leaving the reforming tubes 240 is typically designed to be between 650° C. and 900° C. This synthesis gas is then fed to the oxygen transport membrane tubes 220 filled with one or more catalysts that would facilitate partial oxidation and reforming. Oxygen from the heated intake air permeates through the oxygen transport membrane tubes 220 and facilitates reaction of a portion of the hydrogen and carbon monoxide, and possibly some methane. A portion of the energy or heat generated by this reaction is used for in-situ secondary reforming of the residual methane in the partially reformed synthesis gas 298. The rest of the energy or heat is transferred by radiation to the reforming tubes 240 to drive the primary reforming reactions and by convection to the oxygen-depleted air stream. The synthesis gas 242 leaving the oxygen transport membrane tubes 220, which essentially function as a secondary reformer, is at a temperature between about 900° C. and 1050° C.

The endothermic heating requirements of the reforming process occurring in the primary reforming tubes 240 is supplied through radiation of some of the heat from the secondary reforming oxygen transport membrane tubes 220 together with the convective heat transfer provided by heated retentate stream 224. In addition, as the heated, oxygen depleted retentate stream 224 exits the oxygen transport membrane based reforming system 200, it also heats the mixed feed stream 238 to a temperature between about 475° C. and 650° C. via indirect heat transfer using one or more coils 289 disposed in the retentate stream duct 225.

The synthesis gas stream 242 produced by the oxygen transport membrane based reforming system 200 generally contains hydrogen, carbon monoxide, unconverted methane, steam and carbon dioxide other constituents. A significant portion of the sensible heat from the synthesis gas stream 242 can be recovered using a heat exchange section or recovery train 204. Heat exchange section 204 is designed to cool the produced synthesis gas stream 242 exiting the oxygen transport membrane based reforming system 200. In this illustrated embodiment, the heat exchange section 204 is also designed such that in cooling the synthesis gas stream 242, process steam is generated, hydrocarbon feed stream is preheated, and boiler feed water and feedwater are heated.

The hot synthesis gas 242 is directly cooled to about 400° C. or less in a Process Gas (PG) Boiler 249. The initially cooled synthesis gas stream 244 is then used to preheat the mixture of natural gas and hydrogen feed stream 282 in a pre-heater 250 and subsequently to pre-heat boiler feed water 288 in the economizer 256 and to heat the feed water stream 259. In the illustrated embodiment, the boiler feed water stream 288 is preferably pumped using a feed water pump (not shown), heated in economizer 256 and sent to steam drum 257 while the heated feed water 259 is sent to a de-aerator (not shown) that provides boiler feed water 288. Synthesis gas leaving the feedwater heater 258 is preferably around 160° C. It is cooled down to 38° C. using a fin-fan cooler 261 and a synthesis gas cooler 264 fed by cooling water 266. The cooled synthesis gas 248 then enters a knockout drum 268 where water is removed from the bottoms as process condensate stream 270 which, although not shown, is recycled for use as feedwater, and the cooled synthesis gas 272 is recovered overhead. The cooled synthesis gas stream 272 is optionally compressed in a synthesis gas compressor 274 to produce a synthesis gas product 276. Depending on the operating pressure of the oxygen transport membrane based reforming system, pressure of the recovered synthesis gas is preferably in the range of about 150 and 550 psia and more preferably in the range of 175 and 400 psia.

OTM Based Reformer Reactor and System Corrosion

One of the likely disadvantages of the prior art oxygen transport membrane reforming reactors and systems is the potential for corrosion, and in particular metal dusting corrosion. Metal dusting is a severe form of corrosion that occurs when surfaces of certain metal and metal alloy components and piping are exposed to severe gas environments with a high carbon activity or content. The metal dusting corrosion is manifested by a disintegration of bulk metals, such as iron, nickel and cobalt to metal powders. The typical metal dusting process results from a series of sequential steps, including (i) rapid uptake of carbon into the metallic phase leading to saturation of the alloy matrix with carbon; (ii) formation of metastable carbides; and (iii) decomposition of these carbides into a loose film of carbon and metallic particles, which acts as catalyst for further carbon deposition. The exact mechanism may vary depending on the type of metal being used. The temperatures normally associated with metal dusting are about 400° C. to 800° C. At temperatures generally below 400° C. the rate of reaction to form the metastable carbide species is too low to be significant, while at temperatures above 800° C. the carbon formation is minimal.

To avoid the metal dusting corrosion in the oxygen based transport membrane based reforming system and associated components and piping, the system should be designed to avoid contact of any synthesis gas with metal surfaces having temperatures between about 400° C. to 800° C. While it is possible to provide corrosion resistant coatings on all high temperature metal surfaces exposed to synthesis gas, such solution would be cost prohibitive. The alternative corrosion prevention technique employed in the present embodiments is to manage the temperatures of the synthesis gas so as to avoid contacting bare metal surfaces with synthesis gas in the deleterious temperature range where metal dusting corrosion occurs.

The embodiments illustrated in FIGS. 3 and 4 achieve this temperature control of the metal surfaces exposed to the synthesis gas by preferably recycling the synthesis gas in a high temperature state, generally above 800° C. where the non-recycled portion of the synthesis gas is cooled in the PG boiler until the synthesis gas is cooled below 400° C. The metal surfaces of the synthesis gas piping exiting the oxygen transport membrane based reforming system are either maintained at a temperature above 800° C. or are refractory surfaces. The metal surfaces in the PG boiler and other elements in the heat recovery system that are exposed to the synthesis gas are generally maintained at temperatures below about 400° C.

In the embodiment of FIG. 2, the cooled synthesis gas is recycled back to the oxygen based transport membrane based reactor and the cooled recycled synthesis gas stream is preferably maintained at temperatures below about 400° C. The addition of superheated steam to the recycled synthesis gas stream should be avoided unless the addition of superheated steam maintains the temperatures below about 400° C.

OTM Based Reformer Feed

Figure 6:
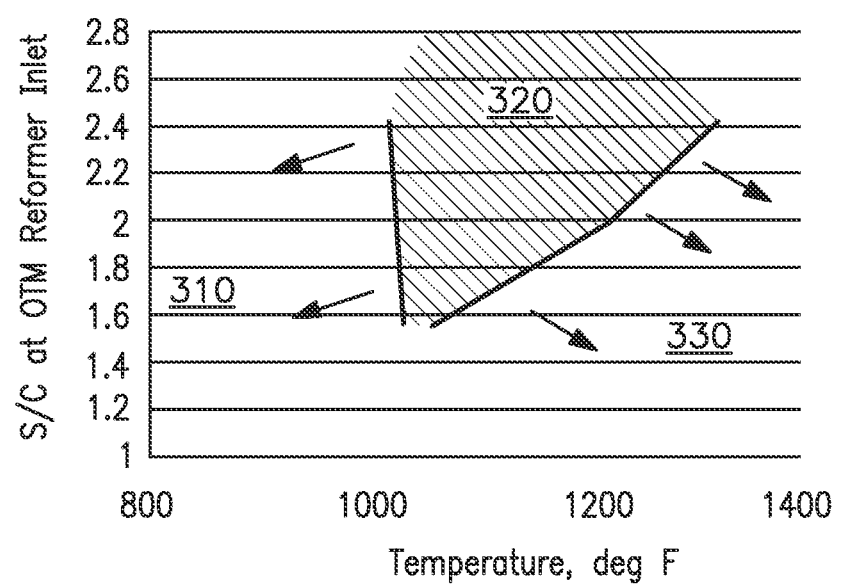
FIG. 6 is a graph of the temperature of a feed stream versus steam to carbon ratio of the feed stream and depicting various performance regimes of an oxygen transport membrane based reforming system.

Turning now to FIG. 6, region 310 on the feed temperature versus feed steam to carbon ratio graph generally corresponds to a combined feed stream at a temperature near or below about 550° C. and having a steam to carbon ratio of between 1.5 and 2.4. Because the present combined feed stream preferably contains carbon monoxide produced in the pre-reformer, a combined feed stream having characteristics of region 310, may undergo unwanted Boudouard reactions thereby depositing excessive amounts of soot on the oxygen transport membrane based reforming system as well as associated components and piping. The Boudouard reaction is a redox reaction of a mixture of carbon monoxide and carbon dioxide at a given temperature and involves the disproportionation of carbon monoxide into carbon dioxide and carbon (i.e. soot).

On the other hand, region 330 generally corresponds to a region of high temperature and low steam to carbon ratios where the combined feed stream is subject to carbon lay down in the reformer tubes, most likely at the inlet. Region 330 is generally depicted as the region to the right of the curve on the feed temperature versus steam to carbon ratio defined by two points, namely a feed temperature near 550° C. with a steam to carbon ratio of 1.5 and a feed temperature of 700° C. with a steam to carbon ratio of 2.4.

It has been found that conditioning the combined feed stream to a particular temperature range and steam to carbon ratio which avoids regions 310 and 330 translates into an optimum operating regime with noticeably less reliability problems in the oxygen transport membrane based reformer system (OTM tubes as well as reformer tubes) due to carbon formation. This window of preferred operating characteristics for the combined feed stream is depicted generally as region 320 in FIG. 6.

As indicated above, the presently disclosed oxygen transport membrane based reforming systems are preferably tailored for use in methanol production plants, either as a retrofit or modification of existing methanol plants or in the design and construction of new methanol plants.

Figure 7:
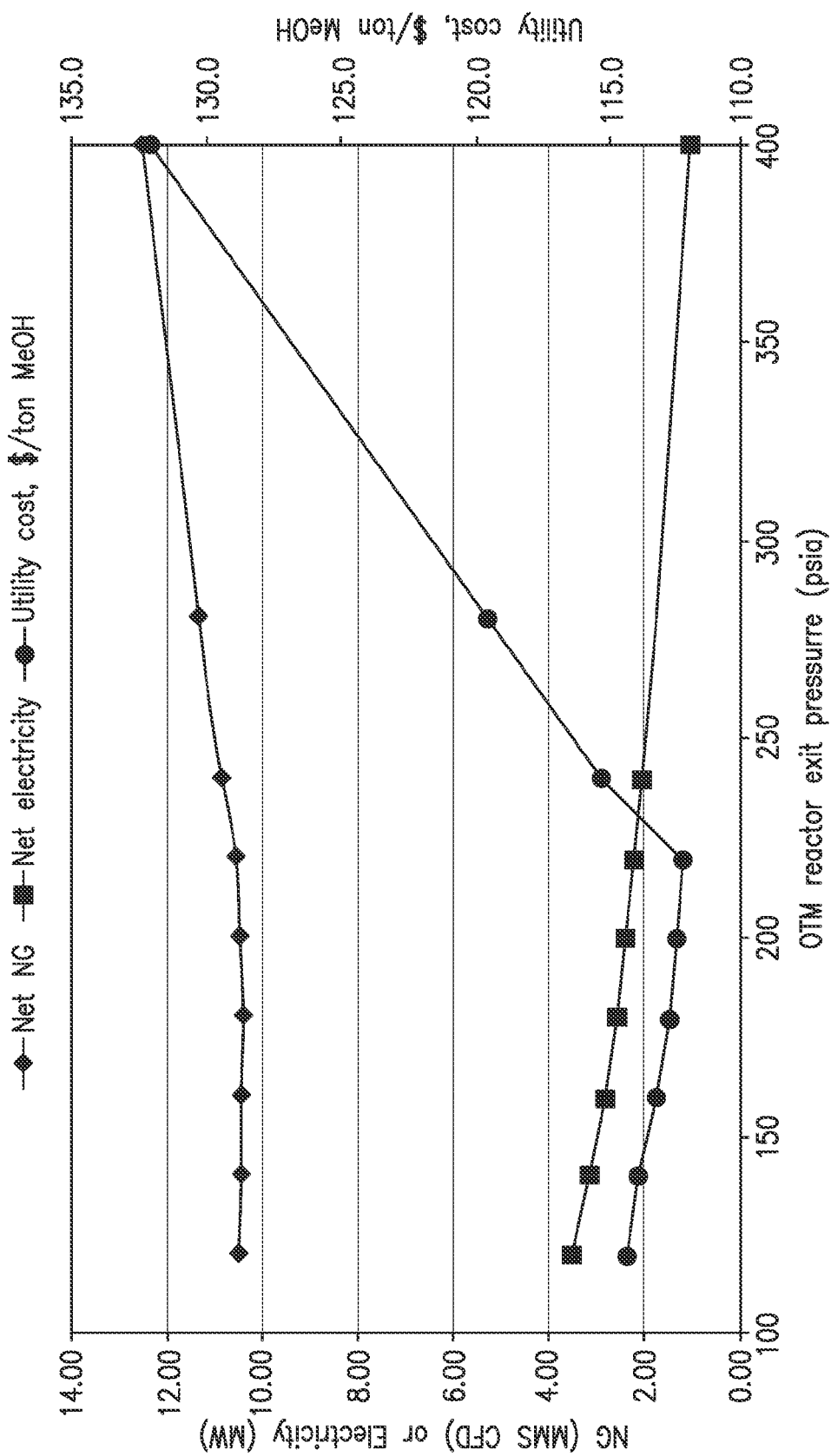
FIG. 7 is a graph for a methanol production application showing the oxygen transport membrane based reactor pressure versus the expected utility consumption rates (NG in MMscfd, electricity in MW) and expected utility costs, expressed in dollars per ton of methanol produced.

As illustrated in the graph of FIG. 7, when the embodiments of the oxygen transport membrane based reforming system described with reference to FIGS. 2-4 are tailored for a methanol production process, the exit pressure of the oxygen transport membrane based reforming system is preferably maintained at a pressure of about 250 psia or less. It has been found, through modeling and estimation, that such pressure range optimizes the overall performance and economics of the oxygen transport membrane based reforming system for methanol production applications. Specifically, when the exit pressure of the oxygen transport membrane based reforming system is maintained at a pressure of about 250 psia or less, the estimated utility cost, expressed in dollars per ton of methanol produced, is optimized at or below about $117, in part due to the low methane slip of less than about 4.5% realized at such exit pressures. A similar curve is observed when one plots the estimated utility cost expressed in dollars per ton of methanol produced versus methane slip. Specifically, when the methane slip is reduced to levels of 4.5% or less, the utility costs are about $117 per ton of methanol produced.

On the other hand, when the embodiments of the oxygen transport membrane based primary and secondary reforming system and reactor described with reference to FIG. 5 are tailored for a methanol production process, the exit pressure of the secondary reformers in the oxygen transport membrane based reforming system are preferably maintained at a pressure of between about 100 psia to about 500 psia. Maintaining the exit pressure of the secondary reformers at the higher pressures within this range (e.g. 400 to 500 psia) optimizes the overall performance and economics of the oxygen transport membrane based primary and secondary reforming reactor and system for methanol production applications. Specifically, when the exit pressure of the of the secondary reformer in oxygen transport membrane based reforming system of FIG. 5 is maintained at about 200 psia, the estimated utility cost, expressed in dollars per ton of methanol produced, is about $113 and when the exit pressure is maintained at about 400 psia, the estimated utility cost is reduced to about $110 per ton of methanol produced.

EXAMPLES

Using the above-described process that employs both an oxygen transport membrane (OTM) based reforming system similar to the embodiments shown in FIG. 2, FIG. 3 and FIG. 5 together with a base SMR synthesis gas production system, three example cases were modeled. All three modeled cases are compared to the base modeled case involving a traditional SMR reactor based methanol plant that is designed to produce 2000 tons/day of methanol. In the base case scenario, the methanol reactor operates at 100% capacity to produce the 2000 tons/day of methanol product and the SMR reactor also is modeled to operate at 100% capacity to supply the synthesis gas needed for the methanol reactor. The required natural gas flow rate to the SMR reactor necessary to operate as suggested above is roughly 61 million scfd. The resulting measure of standard cubic feet (scf) of natural gas (NG) required per ton of methanol produced is roughly 30530 (scf NG/ton MeOH). The comparative results of the modeled cases as shown in Table 1.

In the base modeled SMR only case, the 61 million standard cubic feet per day (scfd) of natural gas is used for both the reformer as well as the burner. At an energy conversion for natural gas of about 1000 BTUs per scf and an estimated cost of about $4 per million BTUs, the total cost of the natural gas is roughly $244,240 per day. In addition, the power requirements for the base SMR case include supplying power to the air blower, boiler feed water pump, synthesis gas/recycle compressor, and methanol product pump which is offset by the power generation associated with the steam expander, liquid expander, and gas expander. As seen in Table 1, the net power consumption for the modeled base case is roughly 7102 kW which, at $45.8 per MWh translates to a power cost of approximately $7,807 per day. Considering only the utility costs (i.e. natural gas, electricity and make-up water), the traditional SMR reactor based methanol plant requires $258,648 per day to operate or roughly $129 per ton of methanol product produced.

The steam to carbon ration in the natural gas feed is roughly 3 resulting in a module of the synthesis gas produced by the base SMR modeled case of about 2.9 and a hydrogen to carbon monoxide ratio of about 5.

Case 1

In Case 1, the base case SMR system is arranged in parallel with an oxygen transport membrane (OTM) based reformer system, similar to the embodiment described above with reference to FIG. 2, to produce the synthesis gas required to increase the methanol production by about 20% or to a total production of about 2400 tons per day of methanol.

In the Case 1 modeled scenario, the 71.52 million cubic feet per hour of natural gas is generally split between the SMR system (61.06 MMscfd), and the OTM based reforming system (10.46 MMscfd), with a portion of the natural gas being used a fuel to fire the burners. The total methanol produced is estimated to be about 2401 tons per day. The steam to carbon ratio in the natural gas feed to the OTM based reforming system is roughly 1.5 resulting in a module of the synthesis gas produced by the combined SMR and OTM arrangement of about 2.7 and a hydrogen to carbon monoxide ratio of about 3.4.

At an energy conversion of about 1000 BTUs per scf of natural gas and an estimated cost of about $4 per million BTUs, the estimated cost of the natural gas for the arrangement in Case 1 is roughly $286,078 per day to produce the 2401 tons of methanol. In addition, the electricity or power requirements for Case 1 is roughly 10694 kW or about $11,755 per day at $45.8 per MWh and includes supplying power to the air blower, boiler feed water pump, synthesis gas/recycle compressor, and methanol product pump and offset by any power generation associated with the steam expander, liquid expander, and gas expander. The total utility costs (i.e. natural gas, electricity and make-up water) for the Case 1 arrangement is roughly $304,602 per day to operate or roughly $115 per ton of methanol product produced which represents a 10.9% lower cost than the base SMR case.

Case 2

In Case 2, the base case SMR system is arranged in parallel with an oxygen transport membrane (OTM) based reformer system, similar to the embodiment described above with reference to FIG. 3, to produce the synthesis gas required to increase methanol production by about 20% or to a total production of about 2400 tons per day of methanol.

In the Case 2 modeled scenario, the 71.58 million cubic feet per hour of natural gas is generally split between the SMR system (61.06 MMscfd), and the OTM based reforming system (10.52 MMscfd), with a portion of the natural gas directed to each system being used a fuel to fire the associated system burners. The total methanol produced is estimated to be about 2400 tons per day. The steam to carbon ratio in the natural gas feed to the OTM based reforming system is roughly 1.5 resulting in a synthesis gas module of about 2.7 with a hydrogen to carbon monoxide ratio of about 3.5.

At an energy conversion of about 1000 BTUs per scf of natural gas and an estimated cost of about $4 per million BTUs, the estimated cost of the natural gas for the arrangement in Case 2 is roughly $286,327 per day to produce the 2400 tons of methanol. In addition, the electricity or power requirements for Case 2 is roughly 9560 kW or about $10,508 per day at $45.8 per MWh and includes supplying power to the air blower, boiler feed water pump, synthesis gas compressor, and methanol product pump and offset by any power generation associated with the steam expander, liquid expander, and gas expander. The total utility costs (i.e. natural gas, electricity and make-up water) for the Case 2 arrangement is roughly $303,609 per day to operate or roughly $112.40 per ton of methanol product produced which represents a 12.9% lower cost than the base SMR case.

Case 3

In Case 3, the base case SMR system is arranged in parallel with an oxygen transport membrane (OTM) based reformer system, similar to the system described above with reference to FIG. 5, to produce the synthesis gas required to increase the methanol production by 20% or to a total production of about 2400 tons per day of methanol.

In the Case 2 modeled scenario, the 72.02 million cubic feet per hour of natural gas is generally split between the SMR system (61.06 MMscfd), and the OTM based reforming system (10.96 MMscfd), with a portion of the natural gas directed to each system being used a fuel to fire the associated system burners. The total methanol produced is estimated to be about 2400 tons per day. The steam to carbon ratio in the natural gas feed to the OTM based reforming system is roughly 2.0 resulting in a module of the synthesis gas produced by the combined SMR and OTM arrangement of about 2.7 with a hydrogen to carbon monoxide ratio of about 3.2.

At an energy conversion of about 1000 BTUs per scf of natural gas and an estimated cost of about $4 per million BTUs, the estimated cost of the natural gas for the arrangement in Case 3 is roughly $288,076 per day to produce the 2399 tons of methanol. In addition, the total net electricity or power requirements for Case 3 is less than the base case at roughly 7042 kW or about $7,759 per day at $45.8 per MWh and includes supplying power to the air blower, boiler feed water pump, synthesis gas compressor, and methanol product pump and offset by any power generation associated with the steam expander, liquid expander, and gas expander. The total utility costs (i.e. natural gas, electricity and make-up water) for the Case 3 arrangement is roughly $302,703 per day to operate or roughly $110.40 per ton of methanol product produced which represents a 14.4% lower cost than the base SMR case.

TABLE 1

|  |  | SMR Base Case | SMR + OTM Case 1 | SMR + OTM Case 2 | SMR + OTM Case 3 |
|---|---|---|---|---|---|
| INPUTS |  |  |  |  |  |
| Natural Gas (NG) | MMscfd | 61.06 | 71.52 | 71.58 | 72.02 |
| Electricity | kW | 7102 | 10694 | 9560 | 7042 |
| Make-Up water | gpm | 1528 | 1567 | 1568 | 1590 |
| OUTPUTS |  |  |  |  |  |
| Methanol | tons/day | 2000 | 2401 | 2400 | 2399 |
| UTILITY COSTS |  |  |  |  |  |
| Natural Gas (NG) | $/day | 244240 | 286078 | 286327 | 288076 |
| Electricity | $/day | 7807 | 11755 | 10508 | 7759 |
| Make-Up water | $/day | 6601 | 6769 | 6774 | 6867 |
| Total Utility Costs | $/day | 258648 | 304602 | 303609 | 302703 |
| COST BASIS |  |  |  |  |  |
| Natural Gas (NG) | $/ton MeOH | 122 | 104 | 105.2 | 109.9 |
| Electricity | $/ton MeOH | 4 | 10 | 6.8 | −0.1 |
| Make-Up water | $/ton MeOH | 3 | 0.4 | 0.4 | 0.7 |
| Total Utility Costs | $/ton MeOH | 129 | 115 | 112.4 | 110.4 |
| RELEVANT PARAMETERS |  |  |  |  |  |
| Overall NG consumption | scf/ton MeOH | 30530 | 29787 | 29826 | 30020 |
| Incremental NG consumption | scf/ton MeOH | — | 26083 | 26304 | 27466 |
| Module of OTM Syngas |  | — | 1.9 | 1.9 | 1.8 |
| Module of SMR/ Combined Syngas |  | 2.9 | 2.7 | 2.7 | 2.7 |
| H2/CO ratio of Syngas |  | 5 | 3.4 | 3.5 | 3.2 |
| S/C ratio in NG Feed |  | 3 | 1.5 | 1.5 | 2.0 |

While the inventions herein disclosed have been described by means of specific embodiments and processes associated therewith, numerous modifications and variations can be made thereto by those skilled in the art without departing from the scope of the invention as set forth in the appended claims or sacrificing all of its features and advantages.

What is claimed is:

1. A method for producing methanol comprising the steps of:
producing a first stream of synthesis gas in a steam methane reformer and/or autothermal reformer by reforming a first hydrocarbon feed stream and a source of steam in the presence of a reforming catalyst;
producing a second stream of synthesis gas in an oxygen transport membrane based reforming system comprising oxygen transport membrane elements by reforming a combined feed stream in the presence of a reforming catalyst and radiant heat generated from the reaction of a hydrogen containing stream contacting a permeate side of said oxygen transport membrane elements and an oxygen permeate produced by the oxygen transport membrane elements from a heated oxygen containing feed stream, the reaction producing a reaction product stream comprising oxidation products, an oxygen depleted retentate stream, and radiant heat, wherein the combined feed stream comprises a second hydrocarbon feed stream, the reaction product stream, and steam;
combining the first stream of synthesis gas and the second stream of synthesis gas to form a combined synthesis gas product stream;
directing the combined synthesis gas product stream to a methanol synthesis reactor;
synthesizing the combined synthesis gas product stream into crude methanol;
recovering excess hydrogen and methane slip during the methanol synthesis;
recycling a portion of the excess hydrogen and methane slip recovered during the methanol synthesis to the oxygen transport membrane based reforming system; and
purifying the crude methanol to a finished methanol product.

2. The method of claim 1 wherein the ratio of the volumetric flow of the first hydrocarbon feed stream to the volumetric flow of the second hydrocarbon feed stream is between about 1.0 and 7.0.

3. The method of claim 1 wherein the combined feed stream has a steam to carbon ratio between about 1.5 and 3.0 and a temperature between about 550° C. and 800° C.

4. The method of claim 1 wherein the combined feed stream has a steam to carbon ratio between about 2.0 and 2.8 and a temperature between about 600° C. and 800° C.

5. The method of claim 1 wherein the second stream of synthesis gas has a module of between about 1.5 and 2.2.

6. The method of claim 1 wherein the second stream of synthesis gas has a hydrogen to carbon monoxide ratio of between about 2.8 and 3.8.

7. The method of claim 1 wherein the second stream of synthesis gas has a methane slip of less than about 4.5 percent by volume.

8. The method of claim 1 wherein the second hydrocarbon feed stream is at a moderate pressure of between about 100 psia and about 250 psia.

9. The method of claim 1 wherein the module of combined synthesis gas stream is between about 2.0 to 2.8.

10. The method of claim 1 wherein a portion of the excess hydrogen recovered during methanol synthesis is recycled to form all or a part of the hydrogen containing stream contacting the permeate side of the oxygen transport membrane.

11. The method of claim 1 wherein a portion of the excess hydrogen and methane slip recovered during methanol synthesis is recycled to the oxygen transport membrane based reforming system to be used as a fuel to heat the oxygen containing feed stream upstream of the oxygen transport membrane.

12. The method of claim 1 further comprising the step of recycling a portion of the excess hydrogen and methane slip recovered during methanol synthesis to the steam methane reformer and/or autothermal reformer.

13. The method of claim 1 further comprising the step of directly cooling the first stream of synthesis gas and/or the second stream of synthesis gas to a temperature of about 400° C. or less.

14. The method of claim 13 further comprising the steps of:
diverting a portion of the cooled second stream of synthesis gas to a shift reactor to undergo a water gas shift reaction;
directing the cooled shifted gas stream to a hydrogen separation unit to produce the hydrogen gas and an off-gas;
combining a portion of the produced hydrogen gas with the remaining portion of the cooled second stream of synthesis gas to produce a combined second stream of synthesis gas having a module between about 2.0 to 2.2.

15. The method of claim 14 wherein the diverted portion of the synthesis gas stream is less than about 20 percent by volume of the cooled second stream of synthesis gas.

16. The method of claim 14 further comprising the steps of:
reheating the oxygen depleted stream to a temperature of between about 1000° C. and 1200° C. using a duct burner disposed within or proximate to the oxygen transport membrane based reforming system, wherein the duct burner is configured to combust a supplemental fuel stream and residual oxygen in the oxygen depleted stream to heat the incoming oxygen containing stream via indirect heat exchange; and
directing a portion of an off-gas to the duct burner to form a portion of the supplemental fuel stream.

* * * * *